United States Patent
Hendriks et al.

(10) Patent No.: US 12,220,273 B2
(45) Date of Patent: Feb. 11, 2025

(54) PERFUSION ANGIOGRAPHY COMBINED WITH PHOTOPLETHYSMOGRAPHY IMAGING FOR PERIPHERAL VASCULAR DISEASE ASSESSMENT

(71) Applicant: KONINKLIJKE PHILIPS N.V., Eindhoven (NL)

(72) Inventors: Bernardus Hendrikus Wilhelmus Hendriks, Eindhoven (NL); Maria-Louisa Izamis, Cambridge, MA (US); Caifeng Shan, Veldhoven (NL)

(73) Assignee: KONINKLIJJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/767,756

(22) PCT Filed: Oct. 13, 2020

(86) PCT No.: PCT/EP2020/078680
§ 371 (c)(1),
(2) Date: Apr. 8, 2022

(87) PCT Pub. No.: WO2021/074097
PCT Pub. Date: Apr. 22, 2021

(65) Prior Publication Data
US 2024/0081766 A1    Mar. 14, 2024

(30) Foreign Application Priority Data
Oct. 14, 2019   (EP) .................................. 19202888

(51) Int. Cl.
A61B 6/00    (2024.01)
A61B 6/46    (2024.01)
(Continued)

(52) U.S. Cl.
CPC .......... *A61B 6/5217* (2013.01); *A61B 6/4417* (2013.01); *A61B 6/463* (2013.01);
(Continued)

(58) Field of Classification Search
CPC ..... A61B 6/5217; A61B 6/4417; A61B 6/463; A61B 6/481; A61B 6/507; A61B 6/5247; A61B 6/5264; G16H 30/40
See application file for complete search history.

(56) References Cited

U.S. PATENT DOCUMENTS

2008/0051648 A1*  2/2008  Suri ..................... A61B 6/5264
                                                                  600/407
2013/0345560 A1* 12/2013  Ferguson, Jr. ..... A61K 49/0034
                                                                  600/431
(Continued)

FOREIGN PATENT DOCUMENTS

EP        3434187       *  1/2019
WO    2007097702 A1       8/2007
(Continued)

OTHER PUBLICATIONS

Jens et al, Perfusion Angiography of the Foot in Patients with Critical Limb Ischemia: Description of the Technique, Cardiovascular Intervention Radiology, vol. 38 (2015) pp. 201-205.*
(Continued)

*Primary Examiner* — Alexei Bykhovski

(57) ABSTRACT

Perfusion angiography combined with photoplethysmography imaging for peripheral vascular disease assessment A device (13) and method for performing perfusion imaging receive image sequences that are acquired simultaneously by an X-ray imaging apparatus (2) and by a photoplethysmography imaging apparatus (3). When temporally aligned, changes in the perfusion states of a perfused organic tissue over time are extracted from the two image sequences and an image is generated for display on a display unit (5) which
(Continued)

indicates the changes in the perfusion states at various locations of the perfused organ tissue, thereby capturing both deep organ tissue and superficial organ tissue perfusion properties. A diminution in an image signal strength in the photoplethysmography images caused by a passage of a bolus comprising a previously administered contrast agent (10) can be used to align the two concurrently acquired image sequences in time.

17 Claims, 1 Drawing Sheet

(51) Int. Cl.
    *A61B 6/50*     (2024.01)
    *G16H 30/40*     (2018.01)

(52) U.S. Cl.
    CPC .............. *A61B 6/481* (2013.01); *A61B 6/507* (2013.01); *A61B 6/5247* (2013.01); *A61B 6/5264* (2013.01); *G16H 30/40* (2018.01)

(56) References Cited

U.S. PATENT DOCUMENTS

2015/0164592 A1*   6/2015   Elhawary ............ A61B 5/0084
                                                                                    600/479
2017/0124768 A1    5/2017   Walle-Jensen
2019/0380807 A1*  12/2019  Addison ............. A61B 5/7425

FOREIGN PATENT DOCUMENTS

| WO | WO 2007097702 | * | 8/2007 |
| WO | 2014001981 A1 | | 1/2014 |
| WO | 2015001427 A2 | | 1/2015 |
| WO | 2016189071 A1 | | 12/2016 |
| WO | WO 2016189071 | * | 12/2016 |

OTHER PUBLICATIONS

International Search Report and Written Opinion of PCT/EP2020/078680, dated Feb. 10, 2021.

Dayan, Lior et al "SPECT/CT-plethysmography-non-invasive quantitation of bone and soft tissue blood flow", Journal of Orthopaedic Surgery and Research, vol. 3, No. 36, 2008.

Jens, Sjoerd et al., "Perfusion Angiography of the Foot in Patients with Critical Limb Ischemia: Description of the Technique", Cardiovascular Intervention Radiology, vol. 38 (2015) pp. 201-205.

Rieß, Henrik Christian et al, Initial experience with a new quantitative assessment tool for fluorescent imaging in peripheral artery disease, VASA, vol. 46, No. 5, pp. 383-388, 2017.

* cited by examiner

PERFUSION ANGIOGRAPHY COMBINED WITH PHOTOPLETHYSMOGRAPHY IMAGING FOR PERIPHERAL VASCULAR DISEASE ASSESSMENT

CROSS-REFERENCE TO PRIOR APPLICATIONS

This application is the U.S. National Phase application under 35 U.S.C. § 371 of International Application No. PCT/EP2020/078680, filed on Oct. 13, 2020, which claims the benefit of European Patent Application No. 19202888.4, filed on Oct. 14, 2019. These applications are hereby incorporated by reference herein.

FIELD OF THE INVENTION

The present invention relates to the field of medical imaging devices and methods. More specifically, the invention relates to devices and methods for imaging vascular tissue of peripheral organs using both perfusion angiography and photoplethysmography.

BACKGROUND OF THE INVENTION

Perfusion angiography represents a widely spread and recognized technique for the assessment of vascular diseases in peripheral organs, as well as treatments thereof. It relies on the study of the perfusion properties of the organic deep tissue that is successfully imaged by contrast-enhanced X-ray imaging such as two-dimensional fluoroscopy. In consequence, perfusion angiography gives valuable insight into the state of health of the perfused tissue, for example in relation to ischemia or revascularization of occluded deep vessels after angioplasty.

European patent specification EP-2866643 discloses a patency evaluating system in which a photoplethysmography (PPG) interpretation module outputs pixel values in an image that represents PPG information collected by a repositionable light sensor from a blood vessel. A PPG map is generated by an image generation module for output to a display. The image generation module is coupled to the PPG interpretation module, thus receiving the output pixels. The light sensor and a light source are mounted on an endoscope such that the light sensor is receiving the light from the blood vessel in response to the light generated by the light source. In one embodiment, the image generation module is configured to overlay the PPG map on an X-ray image.

Embodiments described in this disclosure are directed to the evaluation of patency of a blood vessel that is accessed by an endoscope as typically occurs during (minimal) invasive surgical interventions involving the blood vessel at hand. Therefore, the available information on the perfusion properties of organ tissue is limited or absent.

SUMMARY OF THE INVENTION

Despite the fact of providing quantity of information on the perfusion properties and the health state of the perfused tissue in respect of the peripheral organ's deep vessels, perfusion angiography only delivers limited information on the total perfusion and a more complete three-dimensional perfusion distribution of the perfused organ tissue, in particular on the superficial tissue regions near the surface of the organ. A more complete study relying on the total perfusion properties of the perfused tissue of the peripheral organ would allow for a more accurate assessment of vascular diseases as well as for the elaboration of more effective treatment plans and their monitoring.

The photoplethysmography (PPG) signals collected in respect of a single or a few blood vessels by an endoscopic device configured to achieve this purpose is useful for the assessment of patency during surgical interventions, but this approach is not suitable for the study of perfusion properties related to the whole tissue of an extended peripheral organ such as a limb, e.g. a leg or arm.

It is an object of embodiments of the present invention to provide an imaging method and device that makes information on the overall perfusion properties of a perfused peripheral organ tissue available for study and evaluation, whereby deep perfusion properties of the organ tissue, the tissue microcirculation and superficial organ tissue perfusion near the surface of the organ are revealed.

The above objective is accomplished by a method and device according to the present invention.

In accordance with a first aspect of the present invention, a device for performing perfusion imaging is provided. The device comprises a first input port configured for receiving a first image sequence comprising a plurality of two-dimensional projection images indicative of perfusion states relative to an organ deep tissue being perfused during imaging; a second input port configured for receiving a second image sequence comprising a plurality of two-dimensional photoplethysmography images indicative of perfusion states relative to the organ surface tissue or near surface tissue being perfused during imaging, each of said plurality of photoplethysmography images comprising a plurality of image points associated with blood volume values at a corresponding plurality of distinct spatial locations on the organ surface; a processing unit configured for extracting first and second changes in the perfusion states over time from the received first image sequence and the received second image sequence, respectively, and for aligning the first and second changes in the perfusion states in time, or a quantity derived therefrom; and an output port configured for outputting a perfusion imaging signal for visualizing the aligned first and second changes in the perfusion states, or the quantity derived therefrom.

In a device in accordance with embodiments of the present invention, the processing unit may be configured for aligning the first and second changes in the perfusion states in time by detecting a passage of a previously delivered contrast agent bolus, for instance as a sudden diminution of the blood volume value at one or more image points in the second image sequence.

In a device in accordance with embodiments of the present invention, the processing unit may be configured for deriving, over a predefined region of interest in the organ tissue being perfused during imaging, at least one of the group consisting of an arrival time signal, a time-to-peak signal, a time-density signal from the aligned first and second changes in the perfusion states.

A device in accordance with embodiments of the present invention may further comprise a motion compensation module adapted for cancelling motion artifacts, caused by organ surface tissue or near surface tissue motion during imaging, in the acquired second image sequence.

A device in accordance with embodiments of the present invention may further comprise a third input port for receiving a third image sequence comprising a plurality of two-dimensional fluorescence images indicative of perfusion states relative to the organ surface tissue or near surface tissue being perfused during imaging, and the processing unit may be further configured for extracting third changes in the perfusion states over time from the acquired third image sequence and for aligning the first, second and third changes in the perfusion states in time.

In accordance with a second aspect of the present invention, a perfusion imaging system is described which comprises a device for performing perfusion imaging according to any of the embodiments of the first aspect of the present invention. The perfusion imaging system furthermore comprises an X-ray imaging apparatus for acquiring a first image sequence and a photoplethysmography (PPG) imaging apparatus for acquiring a second image sequence, the X-ray imaging apparatus being coupled to the first input port and the PPG imaging apparatus being coupled to the second input port. Each of the first and the second image sequence comprises a plurality of two-dimensional images; the two-dimensional images of the first image sequence are projection images indicative of perfusion states relative to an organ deep tissue that is to be perfused during imaging and the two-dimensional images of the second image sequence are photoplethysmography images indicative of perfusion states relative to the organ surface tissue or near surface tissue that is to be perfused during imaging. In each of the PPG images, a plurality of image points are associated with blood volume values at a corresponding plurality of distinct spatial locations on the organ surface. The processing unit, also being part of the perfusion imaging system as part of the device for performing perfusion imaging, is configured for initiating simultaneous imaging by the X-ray imaging apparatus and the PPG imaging apparatus, and for extracting first and second changes in the perfusion states over time from the acquired first image sequence and the acquired second image sequence, respectively. Further, the processing unit is configured for aligning the first and second changes in the perfusion states in time, or a quantity derived therefrom. The aligned first and second changes in the perfusion states, or the quantity derived therefrom, are then visualized, in a common image, on a display unit of the perfusion imaging system. The perfusion imaging system may, in embodiments, also includes a delivery device for delivering a contrast agent to the organ tissue that is to be perfused during imaging and the delivery device may be adapted for delivering the contrast agent prior to the simultaneous imaging by the X-ray imaging apparatus and the PPG imaging apparatus.

In accordance with a third aspect of the present invention, a method for imaging perfusion properties relating to a peripheral organ tissue perfusion imaging system is described. Such a method may be performed, for instance, when using the device for performing perfusion imaging according to an embodiment of the first aspect of the present invention, or the perfusion imaging system according to an embodiment of the second aspect of the invention for imaging. The method comprises providing an acquired first image sequence and providing a simultaneously acquired second image sequence. The first image sequence comprises a plurality of two-dimensional X-ray projection images that are indicative of perfusion states relative to an organ deep tissue to be perfused during imaging and the second image sequence comprises a plurality of two-dimensional photoplethysmography (PPG) images that are indicative of perfusion states relative to the organ surface tissue or near surface tissue to be perfused during imaging. Each PPG image is comprising a plurality of image points which are associated with blood volume values at a corresponding plurality of distinct spatial locations on the organ surface. Next, first and second changes in the perfusion states over time are extracted from the acquired first image sequence and the acquired second image sequence, respectively, and the first and second changes in the perfusion states, or a quantity derived therefrom, are aligned in time. An image for display on a display unit is also generated and the generated image comprises a plurality of image signals that are indicating the aligned first and second changes in the perfusion states, or the quantity derived therefrom, at a plurality of perfused organ tissue locations.

Where conventional X-ray angiography only gathers two-dimensional projection images with respect to perfusion properties of deep organ tissue, the combined provision and concurrent use during imaging of the X-ray imaging apparatus and the PPG imaging apparatus is extending the tissue imaging capabilities of the perfusion imaging system in accordance with embodiments of the present invention far beyond the one currently made available in X-ray perfusion angiography and offers insight into the overall perfusion properties of a perfused peripheral organ tissue. It was found that a meaningful interpretation in terms of both deep organ tissue and superficial organ tissue perfusion properties based on the changes in the perfusion states of a perfused organic tissue over time, which are extracted from the two image sequences, is possible if these changes are temporally aligned.

It is an advantage of embodiments of the invention that the overall perfusion properties of a perfused peripheral organ tissue, combining deep perfusion, microcirculatory blush and superficial perfusion, as well as spatial, three-dimensional perfusion distribution information are obtained and made available for analysis by way of a single perfusion imaging system during a single perfusion measurement. This allows for more efficient peripheral vascular disease treatments and their monitoring.

It is an advantage of embodiments of the invention that existing angiography X-ray imaging apparatuses, protocols and software can be easily adapted to account for the simultaneous acquisition of a PPG image sequence.

It is a further advantage of embodiments of the invention that the two-dimensional X-ray imaging technique used in conventional angiography is extended beyond 2D to provide spatial perfusion distributions in three dimensions.

In various embodiments of the invention, a diminution in an image signal strength in the PPG images, caused by a passage of a bolus comprising a previously administered contrast agent delivered by the delivery device of the perfusion imaging system, can be used to align the two concurrently acquired image sequences in time. Hence, it is an advantage of embodiments of the invention that simultaneously acquired image sequence of at least two different imaging modalities, X-ray and PPG, can be accurately aligned in time by detecting a reduction of the image signal amplitude in the image sequence acquired by the PPG imaging apparatus, which reduction is caused by the passage of a previously delivered contrast agent bolus already present in perfusion angiography. No further devices or products are required to achieve the alignment in time. This is a surprising and unexpected finding to the person skilled in the art who would consider the passage of a bolus of contrast material to negatively impact or interfere with the PPG imaging process. In general terms, the PPG image signals are founded on the periodic variations of the light absorption or the light scattering amplitudes in connection with pulsatile blood volume changes at the heartbeat frequency. Any disturbances of the periodic variations or any longer lasting suppression thereof, for example by a maintained interruption or replacement of the blood flow, would provide information that is in conflict with the type of PPG image signals that are commonly expected for arterial oxygen saturation or heartbeat rate measurements. Yet, embodiments of the invention demonstrate that X-ray perfusion angiography imaging and PPG imaging are two imaging techniques that are compatible with each other and for which an interaction mechanism, such as the passage of a bolus, can be beneficial.

In embodiments the method the terms providing of any images may or may not include receiving such images. Receiving of images are meant to include circumstances in which images are not actually generated with the method. For example they may have been obtained from elsewhere, another method and/or another time and are only processed by the current method. The method may indeed include the generation of images and their processing.

The method may be a computer implemented method in which the images are received by the respective inputs of the image processing device and or the system.

In an embodiment of the invention, the processing unit is configured for deriving, over a predefined region of interest in the organ tissue to be perfused during imaging, a quantity from the aligned first and second changes in the perfusion states, wherein the derived quantity is selected from at least one of the group consisting of an arrival time signal, a time-to-peak signal, a time-density signal. The derived quantities, when further studied or visualized on the display unit of the perfusion imaging system, can assist a medical healthcare professional to develop a deeper understanding of the overall perfusion properties of the perfused organ tissue, particularly the dynamic perfusion properties, for example with the goal of developing improved treatment plans.

In various embodiments, the organ that is to be perfused during imaging is a peripheral organ, for example a limb.

In accordance with embodiments of the invention, non-ionic iodinated contrast agent can be delivered by the delivery system of the perfusion imaging system to the peripheral organ tissue at a time preceding the perfusion imaging method. Such contrast agents show only very few side-effects, reducing significantly the health risk of the subject being imaged.

In accordance with embodiments of the invention, the perfusion imaging system may comprise a motion compensation module which is adapted for cancelling motion artifacts, caused by organ surface tissue or near surface tissue motion during imaging, in the acquired second image sequence. Hence, motion artifacts caused by a movement of the peripheral organ, its surface, or parts thereof, which could potentially impact the accuracy of the perfusion imaging system, can be reduced, even minimized, or compensated for.

Embodiments of the invention can be advantageously combined with fluorescent imaging of the perfused organ tissue near the surface of the organ, using a fluorescent agent. This provides additional data on perfusion properties of the peripheral organ for imaging. For such embodiments, the perfusion imaging system may comprise a camera for acquiring a third image sequence which comprises a plurality of two-dimensional fluorescence images. The fluorescent images are indicative of perfusion states relative to the organ surface tissue or near surface tissue to be perfused during imaging. Further, the contrast agent, previously delivered by the delivery device, may comprise a fluorescent agent which is suitable for fluorescent imaging. The processing unit, in accordance with such embodiments, may also be configured for initiating imaging by the camera simultaneously with the X-ray imaging apparatus and the PPG imaging apparatus, for extracting third changes in the perfusion states over time from the acquired third image sequence and for aligning the first, second and third changes in the perfusion states in time.

In yet another aspect, the present invention relates to a computer program product with instructions which, when executed on a data processing device provided with the acquired image sequences as input, cause the data processing device to perform an imaging method in accordance with the third aspect of the invention. The data processing device may be the image processing device as specified herein or the system comprising the data processing device or the image processing device.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

Figure 1:
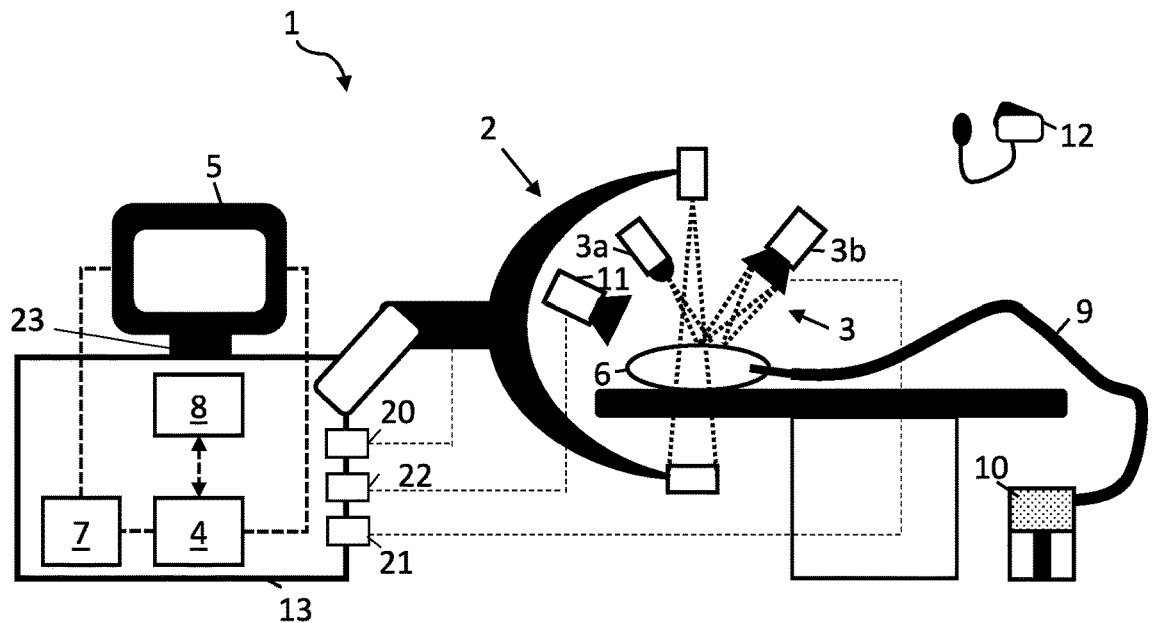
FIG. 1 shows a perfusion imaging system according to one embodiment of the invention.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art.

In the description provided herein, numerous specific details are set forth. However, it is understood that embodiments of the invention may be practiced without these specific details. In other instances, well-known methods, structures and techniques have not been shown in detail in order not to obscure an understanding of this description.

Definitions

In the context of the present invention, perfusion relates to the passage of a body fluid such as blood and lymph through the vascular system and past organs and tissue to maintain their well-functioning. More specifically, perfusion is often characterized in terms of a volume of fluid, such as blood, delivered to an organ or tissue. A perfusion state thus relates to the amount of blood (or other body fluid under study) delivered to the organ or tissue as a function of time and may be expressed, among others, as a flow rate, i.e. the amount or volume of delivered fluid per unit time, or as an integrated amount or volume of delivered fluid over a predetermined time span.

A perfused organ generally refers to a peripheral organ such as a limb, but it may also refer to an inner organ, such as the heart, the brain, an intestine, or a kidney, if exposed during an intervention. Therefore, an organ surface generally refers to the skin and the near surface to the dermis and subcutaneous tissues. For inner organs, however, the exposed organ surface during an intervention can also relate to a tissue structure surrounding the organ, e.g. muscle, fat, or membrane.

The macrocirculation for the purpose of perfusion imaging refers to the arteries of the macrovasculature, whereas the microcirculation refers to arterioles, capillary beds and lymphatic capillaries.

FIG. 1 shows an example of a perfusion imaging system 1 in accordance with an embodiment of the invention. The heart of the perfusion imaging system 1 is a device 13 for performing perfusion imaging, further called a workstation. The perfusion imaging system 1 comprises an X-ray imaging apparatus 2 and a PPG imaging apparatus 3. An organ 6 to be perfused during imaging, for example a peripheral organ such as a limb, e.g. an arm, leg, hand or foot, is positioned relative to the X-ray imaging apparatus 2 and the PPG imaging apparatus 3 in such a way that at least a predefined region of interest of the organ 6 can be imaged simultaneously by the two imaging apparatuses 2, 3. For example, a leg or arm may be positioned on a subject support during perfusion imaging and may be further stabilized by suitable fixation means, such as braces, wedges, sponges, contoured pads, belts, etc. The workstation 13 or a console of the perfusion imaging system 1 is connected at a first input port 20 and a second input port 21, respectively, e.g. directly or over a network, to the X-ray imaging apparatus 2 and the PPG imaging apparatus 3. Thus, in an embodiment, the device 13 is a device for processing perfusion imaging data. The data being generated by the two imaging apparatuses 2 and 3. The first and second input ports can be separate device features, or they can be integrated in a single device feature. The workstation 13 in the illustrated embodiment comprises a processing unit 4, an image merging module 7, and a motion compensation module 8. Simultaneous acquisition by the two imaging apparatuses 2, 3 may be triggered by an acquisition command issued by the processing unit. The X-ray imaging apparatus 2 and the PPG imaging apparatus 3 then acquire each a number of two-dimensional images, e.g. tens to hundreds of images, in parallel and at a predetermined frame rate, e.g. 3 frames per second or more, which can be the same or different for both imaging apparatuses 2, 3. The processing unit 4 is not limited to a single processor or controller, but is used more generally to also describe multiple processors, multiple shared processors, digital signal processors, distributed processing elements, or other suitable data processing means. The processing unit 4 may comprise dedicated hardware for performing the functions in respect of the motion compensation module 8 and the merging module 7, or may be equipped with hardware for executing computer software with segments that perform the defined functionality. Moreover, the processing unit 4 may be provided with its own memory into which the computer software segments, e.g. software modules such as the motion compensation module 8 and the merging module 7, can be loaded and stored. The functional purposes of the motion compensation module 8, as described in more detail further below, is to detect and compensate for motion artefacts at least in the image sequence acquired by the PPG imaging apparatus 3, e.g. uncontrolled motion of the perfused organ or organ surface relative to the PPG imaging apparatus 3. The functional purposes of the merging module 7, as described in more detail further below, is to merge 2D views and 3D views of the same perfused organ.

Although the workstation 13 is shown next to the imaging apparatuses 2, 3, embodiments of the invention are not limited to such a particular arrangement. For instance, the workstation 13 may be installed at a remote location and accessed via a network connection according to other embodiments. Preferably, the workstation 13 also comprises a memory for storing image sequences acquired by the X-ray imaging apparatus 2 and the PPG imaging apparatus 3 during perfusion imaging of the organ 6, previously obtained images or image information in respect of the organ (e.g. previously obtained X-ray scans, magnetic resonance imaging scans, ultrasound scans) if available. Alternatively or additionally, an external memory device may be accessed, e.g. via a network interface, to retrieve or send for storage the image sequences acquired by the X-ray imaging apparatus 2 and the PPG imaging apparatus 3 during perfusion imaging of the organ 6 or the previously obtained images or image information in respect of the organ.

A display unit 5 of the perfusion imaging system 1 may be coupled in any suitable way, e.g. wired or wireless, to an output port 23 of the workstation 13. The display unit 5 may form part of the workstation 13, or may be provided separately. In exemplary embodiments of the invention the display unit 5 may be provided as a display panel, monitor, interactive touch screen, etc. Combined perfusion maps for the organ deep and superficial tissue perfusion properties are displayed by the display unit 5 in a single image.

A delivery device 9 for delivering a contrast agent to the site of the perfused organ deep and superficial tissue is removably connectable to a container filled with a contrast agent 10. By way of example, a delivery device 9 is provided as a catheter and is adapted to be exposed to a blood vessel at one end portion thereof, which blood vessel supplies blood to the perfused organ, to receive a liquid at another end portion thereof, not exposed to the blood vessel, and to deliver the liquid, when received, to the exposed end portion and into the blood vessel. A contrast agent 10 for X-ray perfusion angiography may be provided in a syringe or perfusion pump which is connected to the fluid receiving end portion of the catheter.

A typical PPG imaging apparatus 3 includes a light source 3a for emitting light in the visible spectrum and/or in the infrared spectrum, e.g. a light emitting diode, and a camera 3b for detecting light emitted by the light source 3a and reflected off the organ 6 surface or the organ's near surface during imaging. In a sufficiently bright environment, e.g. bright ambient light strong enough to detect a reflection signal above the noise floor with the camera 3b, the light source 3a may be substituted by the light source generating the bright ambient light. The PPG imaging apparatus 3 enables non-invasive and non-contact imaging of blood volume changes on or closely under the perfused organ surface. In the present example, the PPG imaging apparatus 3 is configured to work in reflection mode and the camera 3b collects the reflected light from the organ surface, e.g. skin, or near surface, e.g. the dermis or subcutaneous tissues, as a plurality of PPG raw signals. For thick peripheral organs such as a leg or an arm, the reflection configuration of the PPG imaging apparatus 3 is the preferred configuration as any transmitted light signal would be strongly attenuated. This does not limit embodiments of the invention to only the reflection configuration of the PPG imaging apparatus 3. The skilled person will understand the fact that the PPG imaging apparatus 3 may be configured to work in transmission mode if the organ 6 to be perfused and imaged is thin, e.g. a finger or a portion thereof, allowing the detection of an observable amount of transmitted light.

A fluorescence imaging camera 11 for detecting fluorescent light, when emitted near the organ's 6 perfused surface tissue by a fluorescent dye comprised by the contrast agent 10, is also part of the perfusion imaging system 1 illustrated in FIG. 1. The fluorescent dye may be excited by a dedicated light source, which may be the same light source as the light source 3a of the PPG imaging apparatus 3, or may be excited by ambient light. The fluorescence imaging camera 11 may advantageously acquire a third image sequence, in addition to and concurrently to the image sequences acquired by the X-ray imaging apparatus 2 and the PPG imaging apparatus 3, from which further perfusion properties of the organ superficial tissue can be inferred. In some embodiments of the invention, the fluorescence imaging camera 11 may be the camera 3a of the PPG imaging apparatus 3 augmented with a switchable colour filter. In other embodiments of the invention, the fluorescence imaging camera 11 may be positioned at a different viewing angle than the camera 3a of the PPG imaging apparatus 3, e.g. may be positioned to face and image an organ surface that is opposite to the organ surface imaged by the camera 3a. The fluorescence imaging camera 11 may be coupled to a third input port 22 of the workstation 13, for delivering its captured image sequence to the processing unit 4 for further processing. Besides, the perfusion imaging system 1 may include a blood retention and release means 12 such as an inflatable cuff. In use, this provides a structure which allows altering an amplitude of the PPG images signals in the images acquired by the PPG imaging apparatus 3.

In the foregoing example, both imaging apparatuses 2, 3 may be combined into a single device or may be provided as separate apparatuses. The latter option is particularly suited for the upgrade of existing X-ray imaging apparatuses 2, which often have a significant installation cost, by supplementing them with the PPG imaging apparatus 3 which can be installed more easily and at a reduced cost. If provided as separate apparatuses, the X-ray imaging apparatus 2 and/or the PPG imaging apparatus 3 may still comprise additional structural elements, and/or the perfusion imaging system 1 may provide an additional assembly, which facilitate the relative positioning, orientation, alignment and stability of the X-ray imaging apparatus 2 and the PPG imaging apparatus 3 during imaging. For instance, the additional structural elements or the additional assembly may comprise holders for the light source 3a and the camera 3b which are coupled to one or more flexible arms having one end fastened to the X-ray imaging apparatus 2 or a wall or ceiling of a room, e.g. of an operating room. Furthermore, embodiments of the invention are not limited to the robotic C-arm X-ray apparatus 2 shown in FIG. 1. Various other X-ray imaging apparatuses 2 can be envisaged and may be provided instead, including robotic or non-robotic devices, computed tomography (CT) X-ray imaging systems, two-dimensional fluoroscopy X-ray imaging devices, and others. In embodiments of the invention, the processing unit 4 may be configured to control the positioning and orientation of the components of the X-ray imaging apparatus 2 and/or the components of the PPG imaging apparatus 3, e.g. relative to the perfused organ 6. Moreover, the processing unit 4 may be configured to control the motion of a robotic delivery device 9 and the injection rate of the contrast agent 10.

Figure 2:
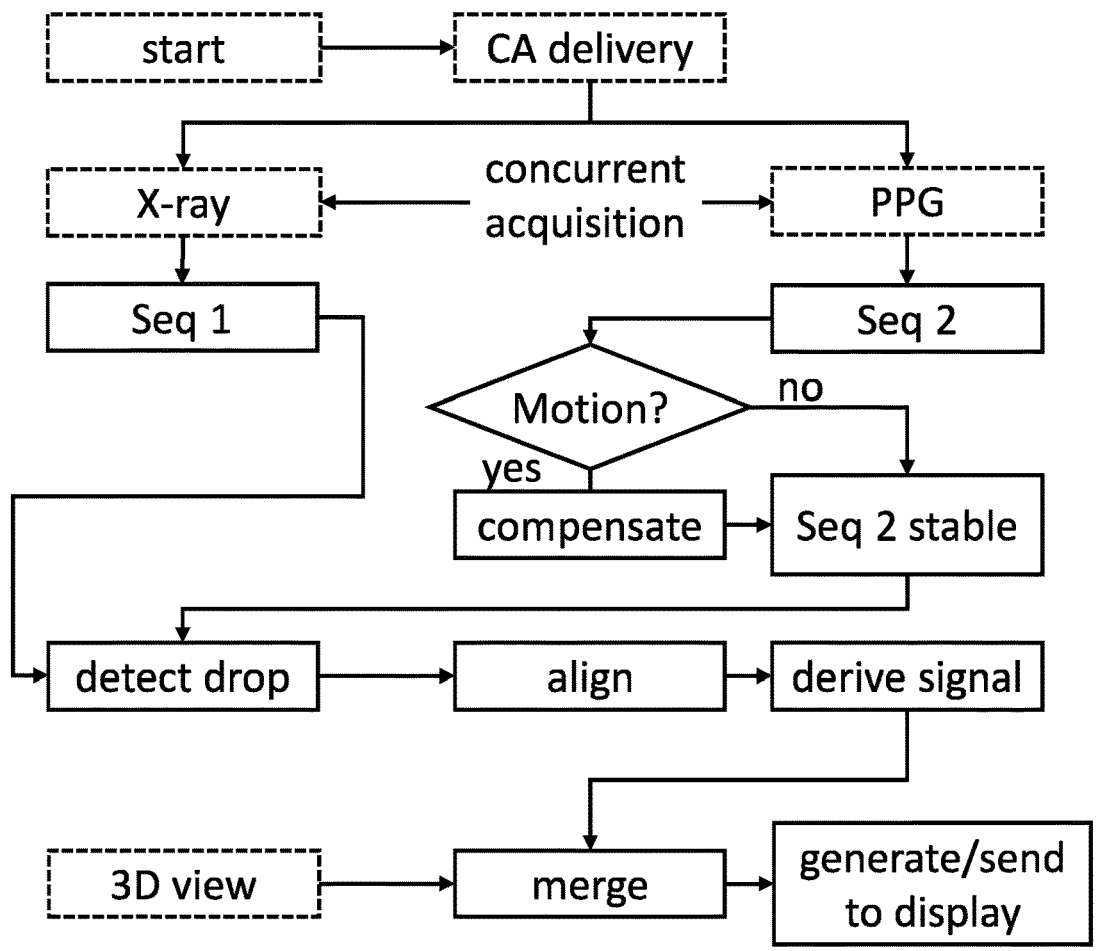
FIG. 2 is a flow diagram explaining the steps of an imaging method of perfusion properties relating to a tissue of a peripheral organ to be perfused in accordance with embodiments of the invention.

A method for imaging perfusion properties relating to a peripheral organ tissue for perfusion, for example the perfused organic tissue of a limb such as a leg or an arm, will now be described with reference to FIG. 2. The steps of the method may often be performed in the context of a more detailed and complex medical procedure, e.g. as part of a pre-operative/post-operative treatment assessment or diagnosis in which it helps assisting healthcare professionals in making their decisions or in revealing diagnostically relevant factors. Some steps of the more detailed medical procedure in the broader context can be of surgical character and immediately precede or follow the method for imaging perfusion properties relating to a peripheral organ tissue for perfusion according to embodiments of the invention. In such cases it shall be understood that the steps that typically precede or follow the method for imaging perfusion properties relating to a peripheral organ tissue for perfusion, or that are performed independently together with said method, are not subject of the invention as defined by the claims. Steps of method for imaging perfusion properties relating to a peripheral organ tissue for perfusion as described in reference to FIG. 2 can be performed by elements of the perfusion imaging system in FIG. 1, described previously. Therefore, the following description may link steps of the methods to individual elements of the perfusion imaging system to provide a comprehensive example of carrying out the method. References to the elements of the perfusion imaging system only have illustrative character and are not limiting the scope of the related imaging method. In the broader context, a medical imaging procedure using embodiments of the method for imaging perfusion properties relating to a peripheral organ tissue for perfusion may be started manually, e.g. a healthcare staff member interacting with the workstation or console to issue a start command, or may be started automatically, e.g. when reaching alignment. This corresponds to the "start" block of the flowchart in FIG. 2. Then a number of steps of the medical imaging procedure, preceding the steps of embodiments of the method for imaging perfusion properties relating to a peripheral organ tissue for perfusion, typically follow: a control signal is issued and transmitted to the delivery device to trigger the injection of a predetermined amount of a contrast agent containing fluid, designated as "CA delivery", and another control signal is issued and transmitted to the X-ray imaging apparatus and the PPG imaging apparatus shortly after to trigger the concurrent acquisition of the first and second image sequences, respectively, designated by the two time-correlated blocks "X-ray" and "PPG". The issue and timing of control signals is typically handled by the processing unit of the workstation, which generates them. The concurrent image acquisition by the X-ray imaging apparatus and the PPG imaging apparatus, and optionally also by fluorescent imaging camera, is generally initiated with a delay with respect to the delivery of the contrast agent by the delivery device to account for the contrast agent bolus to approach the imaged organ tissue region of interest. Such delay is known or can be estimated from existing X-ray angiography imaging protocols. The images of the acquired first and second image sequences, and optionally of a third fluorescence image sequence, are stored on a memory device of the workstation or on a memory device connectable to the workstation for access of the image sequences, e.g. via a network connection. At the time the more general medical imaging procedure starts, the catheter of an exemplary delivery device has already been installed with all due care taken. The administration of the contrast agent is supervised by healthcare professionals and happens prior to the steps of embodiments of the method for imaging perfusion properties relating to a peripheral organ tissue for perfusion. Even administered intravenously at a peripheral location (e.g. popliteal artery), delivering a contrast agent is considered a safe clinical routine procedure, involving only limited, little health risks and accompanying side effects. In particular, allergies based on the agent substance itself can be ruled out by a preparatory evaluation of the patient's personal health status and a corresponding choice of the substance, e.g. non-ionic iodinated contrast materials are widely accepted to present little or no allergic side effects. It is noted that the introduction of a catheter as part of the delivery device and the injection of a contrast agent are not associated with any health risk of a subject if they are performed on a training model of the organ to be perfused or are performed in a virtual training reality environment, for example. Additionally, the supply of blood in the perfused organ may be blocked temporarily, locally or globally, and later be restored by a blood retention and release means, such as a pressure cuff or a compression strip with pressure piece. The associated dynamic changes in the blood volume supplied to the organ tissue that is to be perfused during imaging are observable in the resulting acquired image sequences.

Next, steps of embodiments of the method for imaging perfusion properties relating to a peripheral organ tissue for perfusion are described. The two blocks "Seq 1" and "Seq 2" correspond to the steps of providing the acquired first and second image sequences, respectively. Here, the acquired first image sequence refers to the image sequence which comprises a plurality of two-dimensional X-ray projection images that are indicative of perfusion states relative to the organ deep tissue which has been perfused during imaging and the acquired second image sequence refers to the image sequence which comprises a plurality of two-dimensional PPG images that are indicative of perfusion states relative to the surface tissue or near surface tissue of the same organ perfused during imaging. Each PPG image comprises a plurality of image points, e.g. individual pixels, pixel clusters or segmented image areas, which are associated with blood volume values at a corresponding plurality of distinct spatial locations on the organ surface, e.g. different locations on the skin of a limb, different locations along the leg, ankle and foot, and others. The first and the second image sequences are further characterized by the fact that they were acquired at the same time. The simultaneity of the acquisition can be ascertained, for instance, by overlapping imaging intervals defined by start and end times in a data record structure comprised by or associated with the two image sequences or by comparing the timestamps annotated to each image of the plurality of images of the first and second image sequence. If there exists a third image sequence, e.g. obtained by a fluorescence imaging camera, or even further image sequences, this third or further image sequences can also be provided and the simultaneity of the acquisition thereof can be verified. Providing the image sequences includes directly receiving the acquired images, e.g. as a video stream. For instance, the workstation of the perfusion imaging system is directly connected to the X-ray imaging apparatus and/or the PPG imaging apparatus to receive the acquired images from the apparatus directly as a data stream, e.g. a video stream. Providing the image sequences also includes providing access to a data storage device on which the one or more image sequences are stored. For example, a memory of the workstation may be accessed onto which the first or second imaging sequence, or both, has been sent for storage during the acquisition step. The first and second imaging sequence can also be accessed from a memory device that is remotely connected to the workstation, e.g. a remote server or a distributed storage system, or can be provided as data stored on a computer-readable carrier medium, e.g. on CDs, DVDs, USB devices, optical storage media, flash memory devices, SD cards, magnetic storage media, etc.

The following steps can be executed by the processing unit of the workstation, for instance when following the instructions of a computer program. The processing unit is not limited to a single processor or controller, but is used more generally to also describe multiple processors, multiple shared processors, digital signal processors, distributed processing elements, or other suitable data processing means. The processing unit may comprise dedicated hardware for performing the functions referred to in the following steps or hardware for executing computer software with segments that perform the defined functionality. Moreover, the processing unit may be provided with its own memory into which the computer software segments, e.g. software modules, can be loaded and stored. Preferably, the second image sequence of PPG images, as well as the third image sequence of fluorescence images if provided, is applied to and processed by a motion compensation module for compensating motion artefacts, e.g. a software module of a computer software loaded into a memory of the workstation and instructions of which are executed by the processing unit. Motion artefacts are often caused by unwanted or uncontrolled movements of the perfused organ during imaging, or at least a portion thereof. Small muscular contractions or arterial deformations in response to an increase in the blood pressure, for instance, but also vibrations of the perfusion imaging apparatus reaching the perfused organ via the organ support structure or fixation means can lead to a relative movement of the perfused and imaged organ or its surface with respect to the PPG imaging apparatus, e.g. with respect to a light detecting camera for which a predetermined region of interest has been defined for each image of the second image sequence. If the relative movements become significant, the correspondence between the plurality of image points in each PPG image, e.g. individual pixels, pixel clusters or segmented image areas in each PPG image with which the blood volume values are associated, and the plurality of distinct spatial locations on the organ surface as determined, for instance, in a reference PPG image (e.g. first PPG image of the second image sequence) is lost. This potential loss of correspondence over parts or the entirety of the second image sequence can be remedied by the motion compensation module. To this end, the motion compensation module may be adapted to detect organ or organ surface motion in PPG images which exceed a predetermined threshold, to determine motion vectors for each detected motion in respect of a PPG reference image or in respect of a preceding PPG image, and to compensate for each detected motion by remapping the plurality of image points in each PPG image to the plurality of distinct spatial locations on the organ surface based on the determined motion vectors, thereby restoring the correspondence. Motion estimation algorithms known in the art may be used to achieve the respective steps of the motion compensation module, e.g. motion estimation based on optical flow, on block-matching, on image registration techniques, e.g. comprising feature selection and tracking. If a fluorescence imaging camera provides a third image sequence in addition to the second image sequence provided by the camera of the PPG imaging apparatus, the two cameras may form a stereo camera pair for which corresponding image points, if identified in the acquired third and second image sequence, respectively, can be used to estimate the fundamental matrix, which also allows for motion detection and the determination of motion vectors. If motion of the organ, or a portion thereof, is detected in the second image sequence, this motion is compensated for by the motion compensation module ("compensate") and results in the creation of a stabilized second image sequence, designated as "Seq 2 stable". If no motion is detected, the original second image sequence is used unmodified also as stabilized second image sequence. Idem for the optional third or further image sequences if provided. Embodiments of the invention do not exclude that also the first image sequence can be compensated for motion artefacts if necessary, e.g. to improve more accurately measured perfusion properties.

In a further step, first and second changes in the perfusion states over time are extracted from the acquired first image sequence and the acquired second image sequence, respectively, as well as for each further acquired image sequence that resolves perfusion states of the organ tissue in time. If organ motion has been detected, the acquired and stabilized image sequence is used for the extraction of the corresponding perfusion state changes over time. First perfusion state changes over time may relate to the increasing or decreasing density of the delivered contrast agent that diffuses into and is extracted from the organ deep tissue, e.g. during the first passage. Selecting an X-ray projection images of the first image sequence as X-ray reference image, the first perfusion state changes may be extracted as the measurable, quantified variations of each of a plurality of image signals in each X-ray projection image of the first image sequence in respect of the corresponding plurality of image signals in the X-ray reference image. An image signal of the plurality of so extracted image signals may correspond to individual pixel values or to a group of pixel values, e.g. integrated pixel values over a segmented area or a region of interest in the X-ray projection images of the first image sequence. Hence, for each extracted X-ray image signal defined with respect to the reference X-ray image of the first image sequence, a first time-ordered sequence or time curve can be generated in which an amount of variation of the image signal at a given image number or given image acquisition time, i.e. the extracted first change of the perfusion state over time, is assigned to that given image number or that given image acquisition time. An image acquisition time may be retrieved from an annotated timestamp or may be calculated based on the acquisition start time of the image sequence and the acquisition frame rate, which may be stored in the image sequence data record or in a memory device of the workstation. Second perfusion state changes over time may relate to the increasing or decreasing volume of replaced or diluted blood when the delivered contrast agent reaches, diffuses into, and is extracted from the organ surface tissue or organ near surface tissue, e.g. during the first passage. The replacement or dilution of volumes of blood by the contrast agent are observable as spatially resolved variations in each of a plurality of image signals for each PPG image of the second image sequence, provided a PPG reference signal has been selected. In analogy to the first extracted changes of the perfusion state over time for the acquired first image sequence, an image signal of the plurality of extracted image signals for each PPG image may correspond to individual pixel values or to a group of pixel values, e.g. integrated pixel values over a segmented area or a region of interest in the PPG images of the second image sequence. Hence, for each extracted PPG image signal defined with respect to the reference PPG image of the second image sequence, a second time-ordered sequence or time curve can be generated. It is often useful to extract an envelope signal for each PPG image signal because the various PPG image signals are typically characterized by an oscillating amplitude, which is a consequence of the blood pressure oscillations at the frequency of the heartbeat. Next, a "detect drop" step detects a reduction in the amplitude of the X-ray image signals and of the PPG signals or extracted PPG envelop signals. This reduction of the amplitude may be detected as a decrease below a predetermined threshold, as a decrease equal to or larger than a predetermined signal amplitude ratio, or as a decrease equal to or larger than a predetermined slope of the time curves, for example. At its first passage through the perfused organ tissue, the contrast agent appears as a concentrated bolus which, upon reaching the macro- and microvasculature of the perfused organ, rapidly replaces the blood circulating therein, whereby the blood volume detectable by the PPG imaging apparatus suddenly drops as well as the amount of X-rays reaching an X-ray detector of the X-ray imaging apparatus without undergoing absorption. Since the signal amplitudes for both the X-ray signals and the PPG signals are reduced, the sudden reduction can advantageously serve as an alignment marker for temporally aligning the extracted first and second changes in the perfusion states over time, e.g. aligning the X-ray signal and PPG (envelope) signals in time. The alignment step "align" of the extracted first and second changes may include comparing the time values in portions of organ deep tissue at which the reduction/drop is first detected with the time values in corresponding adjacent portions of organ surface or near surface tissue at which the reduction/drop is first detected. For example, visually identified or algorithmically identified adjacent portions of deep and superficial tissue of the perfused organ, e.g. by using image registration on contoured images, can be analyzed for the first occurrence of an abrupt reduction of the amplitude in the extracted first change and extracted second change, respectively. If the detected time values for the first and second acquired image sequences do not match, either one of the first or second image sequence may be shifted forward or backward in time, homogeneously lowering or increasing the time values assigned to each of the images of the shifted image sequence, until there is a match and the two image sequences are temporally aligned. The alignment step may comprise interpolating between two or more acquired images of the first and/or second image sequence to obtain a more precise alignment in time, e.g. if the two frame rates for acquisition are different or if a diffusion time constant between deep tissue and superficial tissue is taken into account.

A contrast agent also comprising a fluorescent compound will lead to a sudden increase in the amount of fluorescence light captured by the fluorescence imaging camera acquiring the third image sequence. Therefore, if the third image sequence is provided, the fluorescence image signals in the images of the third image sequence are preferably aligned with the X-ray signals and the PPG image signals by detecting a burst or spike instead of a drop.

In the "derive signal" step, various quantities relating to perfusion properties of the organ tissue may be derived from the aligned X-ray and PPG time curves, e.g. the time curves can be averaged or integrated over a predetermined region of interest, or an arrival time or a peak time in the magnitude of the time curves can be determined. Embodiments of the invention are not limited to the specific quantities listed as examples and other quantities for assessing changes in the perfusion states may prove useful. For instance, a perfusion propagation speed may be estimated based on a discrete differentiation of the extracted and aligned X-ray and PPG time curves and a plurality of thresholds applied to distinguish between high, normal and slow propagation speed.

During the "merge" step, a previously obtained 3D view of the organ that is perfused during the perfusion imaging, if available, is merged with the obtained 2D views of the perfusion properties, i.e. the extracted two-dimensional image signals in the temporally aligned first and (stabilized) second image sequences or any derived quantity thereof. A 3D view of the organ may be obtained ("3D view" step) as a 3D reconstruction of a previously acquired three-dimensional image data set, e.g. CT projection data from a pre-operative CT scan of the same organ. The 3D view of the organ may be stored as a 3D object data on a memory device of the workstation or accessible to the workstation. The merging of the 2D views with the previously obtained 3D view generates a correspondence between data points in the 3D object data for the 3D view (e.g. voxels in 3D space or pixels in 2D projection spaces) and the data points relating to the 2D views (e.g. pixel elements or contours of segmented regions in the various temporally aligned X-ray projection images of the first image sequence and PPG images of the second image sequence). Known 2D/3D image registration algorithms (e.g. rigid or non-rigid or affine transformation, point-set matching, feature-based meshes, etc.) may be provided to this end and the 2D images of the first or second image sequence may be resampled at a higher resolution if so required. As a result of the merging step, the PPG image signals which relate to the points on or immediately under the organ surface (e.g. skin), which is a two-dimensional surface in 3D space, can be linked to data points (e.g. voxels) in a 3D view of the organ that also represent the outer surface of the organ, thereby obtaining a missing depth component.

An image for view on a display is generated in the step "generate/send to display" and transmitted to a display unit, e.g. to a display of the workstation. The processing unit, which may comprise a dedicated graphical processor, is generating the image based on the combined perfusion map, e.g. generates a color-coded heat map for representing, on a common scale, the magnitude of the temporally aligned first and second changes of the perfusion states of the organ deep and superficial tissue at various pixel elements of the image to be displayed. Preferably, the image for display is generated by using a 2D/3D blending algorithm such as alpha-blending to determine the color value at each pixel element of the image if the image generated is the result of a combination of 2D and 3D views of the perfused organ. For example, the processing unit may determine the saturation value or an alpha-channel value of each pixel as a function of a scene lighting, a viewing perspective, and depth-overlapping image objects (e.g. overlapping polygons of meshed objects). This allows for the generation of image for display in which the color-coded combined perfusion map is illustrated as an overlay image to a 3D reconstruction image of the organ, using the established correspondences between 3D views and 2D views of the organ as provided by the merging module. Presenting the combined perfusion map as an overlay image to the 3D reconstruction of the organ facilitates orientation and improves the visual inspection experience by the person viewing the image. The image may further be generated interactively so as to provide regular image updates to the viewing person in response to changing viewing conditions, e.g. when interactively rotating the 3D reconstruction image with the combined perfusion map overlay according to different viewing angles, when interactively selecting a perfused organ tissue portion (e.g. skin or deep tissue) to be enabled or disabled in the displayed image, or when interactively switching between different derived quantities (e.g. time-to-peak, time-to-arrival, area under curve, etc.) that reflect changes in the aligned first and second changes of the perfusion state over time.

Embodiments of the invention can be successfully applicable in medical screening, diagnosis and treatment procedures for peripheral arterial diseases, in particular for critical limb ischemia (CLI) for which the proposed perfusion imaging system and method may positively assist in critical decision taking, such as deciding to perform an amputation or a revascularization intervention. Conventional risk assessment factors for CLI, e.g. blood pressure measurements and the related ankle pressure or ankle-brachial index, may provide data on the health status of the macrovasculature, but which may account for artery calcification only imprecisely or insufficiently. Also, the health status of the microcirculation remains undetected although it is important for good tissue perfusion. In the context of CLI, the organ to be perfused may be a leg and a predetermined region of interest may correspond to a region defined around the ankle and the foot. Then the X-ray imaging apparatus and the PPG imaging apparatus acquire a first image sequence of X-ray angiography projection images and a second sequence of PPG images simultaneously, thereby capturing the passage, diffusion and extraction of the delivered contrast agent in the organ deep tissue and superficial tissue within the region of interest over time. These changes in the perfusion states of the organ deep tissue and superficial tissue over time are represented by the time-varying image signals in the X-ray projection images of the first image sequence and the PPG images of the second image sequence, respectively. Therefore, extracting the time-varying image signals in the X-ray projection images of the first image sequence and the PPG images of the second image sequence allows for a successful mapping of the organ tissue perfusion below the skin as well as skin perfusion over time. To combine and correlate the two perfusion measurements, one on deep tissue perfusion and the other on superficial skin perfusion, the various extracted time-varying image signals in the X-ray projection images of the first image sequence and the PPG images of the second image sequence are aligned in time. This can be achieved, for example, by detecting the moment in time at which a sudden diminution of the time-varying image signal amplitudes in the X-ray projection images, integrated over the region of interest, takes place and comparing it to a similarly detected moment in time at which a sudden diminution of the time-varying image signal amplitudes in the PPG images, integrated over the region of interest, occurs. If the comparison shows that the two moments of time differ from each other, either one of the first image sequence or the second image sequence is shifted in time to make the two moments in time equal to each other. For example, the timestamps of the annotated images of the first or second image sequence are collectively increased or decreased until the two moments in time match. From the aligned time-varying image signals in the X-ray projection images and the PPG images various quantities can be derived. For example, time-density curves for the region of interest may adequately express the changes in the perfusion states under the skin and at the skin, respectively. The time-density curve are obtained by integrating the image signals in the X-ray projection images as well as the image signals in the PPG images over the region of interest. The two time-density curves can be combined into a single graph and presented to the physician. It is also possible to integrate the area under the time-density curves obtained for each pixel in the region of interest, e.g. from each image signal in the X-ray projection images as well as from each related image signal in the PPG images within the region of interest. Another quantity of interest that can be derived for quantifying a perfusion state of organ deep and superficial tissue is the time-to-peak intensity. An image may then be generated and displayed, which image shows the derived quantity of interest as a combined perfusion map to the physician, e.g. represented as color-coded perfusion map (heat map) of the foot and ankle. In preferred embodiment, a previously obtained 3D X-ray image of the organ is augmented with the combined perfusion map as overlay, which facilitates spatial orientation and visual inspection of the results shown in the displayed perfusion map. The displayed map illustrates whether the circulatory flow is, for example, within a normal velocity range (time-to-peak), or has a pathologic decline in velocity from ankle to toes, or whether there is some evidence of blush. In addition thereto, the displayed map is also capable of resolve the 3D distribution of the macro- and microcirculatory flow, e.g. it adequately shows whether the skin surface of the foot has been perfused where a wound may be located, e.g. an ulcer in need of an increased blood supply for healing, or where a wound may be at risk of developing.

In embodiments of the invention, the contrast agent delivered by the delivery device may comprise non-ionic iodinated contrast material (e.g. iodixanol 320 mg iodine/ml), which has the advantage of diffusing significantly into the interstitial space of the perfused organ during the first pass, thereby allowing improved detection of the perfusion properties of the microcirculation. Preferably, the non-ionic iodinated contrast material is combined with a fluorescent agent such as a fluorescent dye, e.g. indocyanine green (ICG). This allows for the simultaneous acquisition of PPG images and of fluorescence images by a fluorescence imaging camera, i.e. a camera detecting the fluorescent light emitted by the dye, to further monitor the organ superficial tissue perfusion properties, e.g. the perfusion of the skin. The wash in and the wash out of the dye molecules in the organ superficial tissue is detected in this way.

In embodiments of the invention, the PPG imaging apparatus may be used without the X-ray imaging apparatus for the acquisition of additional image sequences of PPG images, for example in combination with a temporary blocking of blood flowing into the perfused organ by a pressurized cuff, followed by a restored blood flow into the perfused organ upon release of the cuff. A restricted blood flow caused by the pressurized cuff induces a diminution of the PPG image signal amplitudes that is similar, but not identical to the one of the passage of the contrast agent bolus. For instance, the well-controlled pressurization, e.g. inflation, and depressurization, e.g. deflation, rates of a pressurized cuff may be used in an advantageous manner to create blood flow patterns in many different ways not obtainable with the passage of a bolus. A non-limiting example of flow patterns created in that way is the slow release of the cuff pressure versus the fast decrease of the cuff pressure, which provides additional insight into the organ's perfusion properties evolving at different timescales. Furthermore, it is an advantage that the cuff can be pressurized and depressurized repeatedly and with controlled pauses, whereas the possibility of multiple passages of the bolus of contrast agent material is very limited by the spreading and the decrease in concentration for multiple passages of a same administered bolus on the one hand and by the burden imposed on the subject, especially on the subject's kidney, for multiple administered boluses on the other hand.

Further, embodiments of the invention may acquire the X-ray projection images of the first image sequence as subtraction images with enhanced contrast, e.g. the X-ray imaging apparatus of the perfusion imaging system is configured to operate in the digital subtraction angiography (DSA) mode.

While the invention has been illustrated and described in detail in the drawings and foregoing description, such illustration and description are to be considered illustrative or exemplary and not restrictive. Other variations to the disclosed embodiments can be understood and effected by those skilled in the art in practicing the claimed invention, from a study of the drawings, the disclosure and the appended claims. The mere fact that certain measures are recited in mutually different dependent claims does not indicate that a combination of these measures cannot be used to advantage. Any reference signs in the claims should not be construed as limiting the scope.

The invention claimed is:

1. A device for processing perfusion images, the device comprising:
    a processor in communication with memory, the processor configured to:
        receive a first image sequence comprising a plurality of X-ray angiography images indicative of first perfusion states relative to deep tissue of an organ,
        receive a second image sequence comprising a plurality of two-dimensional photoplethysmography images indicative of second perfusion states relative to surface tissue or near surface tissue of the organ, each of the plurality of two-dimensional photoplethysmography images comprising a plurality of image points associated with blood volume values at a corresponding plurality of distinct spatial locations on a surface of the organ,
        extract first changes in the first perfusion states over time from the received first image sequence and second changes in the second perfusion states over time from the received second image sequence,
        align the first changes in the first perfusion states and the second changes in the second perfusion states, or a quantity derived therefrom, in time by detection of a reduction of image signal amplitude in the second image sequence of the plurality of two-dimensional photoplethysmography images caused by a passage of a previously delivered contrast agent bolus, and
        output a perfusion imaging signal for visualizing the aligned first changes and second changes, or the quantity derived therefrom.

2. The device according to claim 1, wherein the processor is further configured to derive, over a predefined region of interest of the organ, at least one of an arrival time signal, a time-to-peak signal, and a time-density signal from the aligned first changes and second changes.

3. The device according to claim 1, wherein the processor is further configured to cancel motion artifacts, caused by motion of the surface tissue or the near surface tissue during imaging, in the second image sequence.

4. The device according to claim 1, wherein the processor is further configured to:
    receive a third image sequence comprising a plurality of two-dimensional fluorescence images indicative of third perfusion states relative to the surface tissue or the near surface tissue,
    extract third changes in the third perfusion states over time from the third image sequence, and
    align the first changes in the first perfusion states, the second changes in the second perfusion states, and the third changes in the third perfusion states.

5. A perfusion imaging system comprising:
    the device for processing perfusion images according to claim 1,
    an X-ray imaging apparatus configured to acquire the first image sequence, the X-ray imaging apparatus connectable to a first input port of the device configured to receive the first image sequence,
    a photoplethysmography imaging apparatus configured to acquire the second image sequence, the photoplethysmography imaging apparatus connectable to second input port of the device configured to receive the second image sequence,
    the processor configured to initiate simultaneous imaging by the X-ray imaging apparatus and the photoplethysmography imaging apparatus, and
    a display configured to visualize, in a common image, the aligned first changes and second changes, or the quantity derived therefrom, the display connectable to an output port of the device.

6. The perfusion imaging system according to claim 5, wherein:
    the processor is further configured to map the aligned first changes and second changes, or the derived quantity therefrom, to a three-dimensional reconstruction image of the organ, and
    the display is configured to display the mapped aligned first changes and second changes, or the derived quantity therefrom, as an overlay image to the three-dimensional reconstruction image of the organ.

7. The perfusion imaging system according to claim 5, wherein the photoplethysmography imaging apparatus comprises a light source for emitting light in at least one of a visible spectrum and an infrared spectrum, and a camera configured to detect light emitted by the light source and reflected off the surface tissue or the near surface tissue during imaging.

8. The perfusion imaging system according to claim 5, further comprising a camera configured to acquire a third image sequence comprising a plurality of two-dimensional fluorescence images indicative of perfusion states relative to the surface tissue or the near surface tissue, the camera connectable to a third input port of the device.

9. The perfusion imaging system according to claim 5, further comprising an inflatable cuff configured to cause a measurable diminution of the blood volume value at one or more image points in the second image sequence during imaging.

10. The method according to claim 1, further comprising:
deriving, over a predefined region of interest of the organ, at least one of an arrival time signal, a time-to-peak signal, and a time-density signal from the aligned first changes and second changes.

11. A method for processing perfusion images, the method comprising:
    providing a first image sequence comprising a plurality of X-ray angiography images indicative of first perfusion states relative to deep tissue of an organ being perfused during imaging, and
    providing a second image sequence comprising a plurality of two-dimensional photoplethysmography images indicative of second perfusion states relative to surface tissue or near surface tissue of the organ being perfused during the imaging, each of the plurality of two-dimensional photoplethysmography images comprising a plurality of image points associated with blood volume values at a corresponding plurality of distinct spatial locations on a surface of the organ, extracting first changes in the first perfusion states over time from the first image sequence and second changes in the second perfusion states over time from the second image sequence, aligning the first changes and the second changes, or a quantity derived therefrom, in time by detecting a reduction of image signal amplitude in the second image sequence of the plurality of two-dimensional photoplethysmography images caused by a passage of a previously delivered contrast agent bolus, and generating an image for display, the image comprising a plurality of image signals indicating the aligned first changes and second changes, or the quantity derived therefrom, at a plurality of perfused organ tissue locations.

12. The method according to claim 11, further comprising:

providing a third image sequence, acquired simultaneously with the first image sequence and the second image sequence, the third image sequence comprising a plurality of two-dimensional fluorescence images indicative of third perfusion states relative to the surface tissue or near surface tissue being perfused during the imaging, extracting third changes in the third perfusion states over time from the third image sequence, and aligning the first changes, the second changes, and the third changes.

13. The method according to claim 11, further comprising:

applying motion compensation at least to the plurality of two-dimensional photoplethysmography images of the second image sequence to cancel motion artifacts caused by the surface tissue or the near surface tissue moving during the imaging.

14. A non-transitory computer-readable storage medium having stored a computer program comprising instructions which, when executed by a processor, causes the processor to:

receive a first image sequence comprising a plurality of X-ray angiography images indicative of first perfusion states relative to deep tissue of an organ;

receive a second image sequence comprising a plurality of two-dimensional photoplethysmography images indicative of second perfusion states relative to surface tissue or near surface tissue of the organ, each of the plurality of two-dimensional photoplethysmography images comprising a plurality of image points associated with blood volume values at a corresponding plurality of distinct spatial locations on a surface of the organ;

extract first changes in the first perfusion states over time from the received first image sequence and second changes in the second perfusion states over time from the received second image sequence;

align the first changes in the first perfusion states and the second changes in the second perfusion states, or a quantity derived therefrom, in time by detection of a reduction of image signal amplitude in the second image sequence of the plurality of two-dimensional photoplethysmography images caused by a passage of a previously delivered contrast agent bolus; and output a perfusion imaging signal for visualizing the aligned first changes and second changes, or the quantity derived therefrom.

15. The non-transitory computer-readable storage medium according to claim 14, wherein the instructions, when executed by the processor, further cause the processor to: derive, over a predefined region of interest in tissue of the organ, at least one of an arrival time signal, a time-to-peak signal, and a time-density signal from the aligned first changes and second changes.

16. The non-transitory computer-readable storage medium according to claim 14, wherein the instructions, when executed by the processor, further cause the processor to: apply motion compensation at least to the plurality of two-dimensional photoplethysmography images to cancel motion artifacts, caused by motion of the surface tissue or the near surface tissue during imaging, in the second image sequence.

17. The non-transitory computer-readable storage medium according to claim 14, wherein the instructions, when executed by the processor, further cause the processor to:

receive a third image sequence comprising a plurality of two-dimensional fluorescence images indicative of third perfusion states relative to the surface tissue or the near surface tissue, extract third changes in the third perfusion states over time from the third image sequence, and align the first changes in the first perfusion states, the second changes in the second perfusion states, and the third changes in the third perfusion states.

\* \* \* \* \*